United States Patent
Taylor (10) Patent No.: US 11,241,319 B2
(45) Date of Patent: *Feb. 8, 2022

(54) METHOD AND DEVICE FOR ORDERING A CUSTOM ORTHOPEDIC DEVICE

(71) Applicant: OSSUR HF, Reykjavik (IS)

(72) Inventor: Jason Robert Taylor, Foothill Ranch, CA (US)

(73) Assignee: OSSUR HF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 17/178,643

(22) Filed: Feb. 18, 2021

(65) Prior Publication Data

US 2021/0169665 A1 Jun. 10, 2021

Related U.S. Application Data

(63) Continuation of application No. 14/011,300, filed on Aug. 27, 2013, now abandoned.

(60) Provisional application No. 61/694,314, filed on Aug. 29, 2012.

(51) Int. Cl.
  *A61F 2/50* (2006.01)
  *A61F 5/01* (2006.01)

(52) U.S. Cl.
  CPC .......... *A61F 2/5044* (2013.01); *A61F 5/0106* (2013.01); *A61F 5/0123* (2013.01)

(58) Field of Classification Search
  CPC ..... A61F 2/5044; A61F 5/0106; A61F 5/0123
  See application file for complete search history.

(56) References Cited

U.S. PATENT DOCUMENTS

| | | | |
|---|---|---|---|
| 399,167 | A | 3/1889 | Starrett |
| 1,007,229 | A | 10/1911 | Nielsen |
| 1,294,723 | A | 2/1919 | Swinburne |
| 1,621,526 | A | 3/1927 | Culell |
| 2,318,864 | A | 5/1943 | Jackson |
| 2,980,110 | A | 4/1961 | Brumfield et al. |
| 3,008,239 | A | 11/1961 | Lange |
| 3,140,546 | A | 7/1964 | Bartlett |
| 3,953,900 | A | 5/1976 | Thompson |
| 4,008,523 | A | 2/1977 | Von Voros |
| 4,315,372 | A | 2/1982 | Kinkead |
| 4,776,327 | A | 10/1988 | Russell |

(Continued)

OTHER PUBLICATIONS

"Omega: Omega Tracer is the most versatile CAD/CAM technology for the orthotic and prosthetic industry." Downloaded from https://web.archive.org/web/20130513201657/http://www.willowwoodco.com/products-and-services/omega, May 13, 2013, 42 pages.

(Continued)

*Primary Examiner* — Boubacar Abdou Tchoussou
(74) *Attorney, Agent, or Firm* — Workman Nydegger (57) ABSTRACT

A method and device for digital measuring and ordering a custom orthopedic device includes an interactive method intended to assist clinicians select, measure and submit precise specifications for patients requiring custom orthopedic devices. The method includes a plurality of menus permitting the clinician to input specifications and submit orders electronically with the specifications and other data packaged together. The method and device include visualization indications to appropriately ensure image capture of a limb from various angles, including posterior, anterior, lateral and medial angles.

14 Claims, 4 Drawing Sheets

(56) References Cited

U.S. PATENT DOCUMENTS

| | | | |
|---|---|---|---|
| 4,807,605 A | 2/1989 | Mattingly | |
| 4,827,916 A | 5/1989 | Kosova | |
| 4,843,720 A | 7/1989 | Kim | |
| 5,038,795 A | 8/1991 | Roush et al. | |
| 5,443,510 A | 8/1995 | Shetty et al. | |
| 5,556,373 A | 9/1996 | Motloch | |
| 5,662,594 A | 9/1997 | Rosenblatt | |
| 5,741,215 A | 4/1998 | D'Urso | |
| 5,768,134 A | 6/1998 | Swaelens et al. | |
| 5,857,987 A | 1/1999 | Habermeyer | |
| 5,880,964 A | 3/1999 | Schall et al. | |
| 5,888,216 A | 3/1999 | Haberman | |
| 5,911,126 A * | 6/1999 | Massen | G06T 7/593 702/153 |
| 6,236,743 B1 | 5/2001 | Pratt | |
| 6,427,695 B1 | 8/2002 | Zanetti et al. | |
| 6,463,351 B1 | 10/2002 | Clynch | |
| 6,540,708 B1 | 4/2003 | Manspeizer | |
| 6,553,685 B2 | 4/2003 | Nishina et al. | |
| 6,564,086 B2 | 5/2003 | Marchitto et al. | |
| 6,572,571 B2 | 6/2003 | Lowe | |
| 6,597,965 B2 | 7/2003 | Graves et al. | |
| 6,613,006 B1 | 9/2003 | Asherman | |
| 6,613,716 B2 | 9/2003 | Hoefs et al. | |
| 6,725,118 B1 | 4/2004 | Fried et al. | |
| 6,726,641 B2 | 4/2004 | Chiang et al. | |
| 6,968,246 B2 | 11/2005 | Watson et al. | |
| 7,127,101 B2 | 10/2006 | Littlefield et al. | |
| 7,210,926 B2 | 5/2007 | Tadros et al. | |
| 7,242,798 B2 | 7/2007 | Littlefield et al. | |
| 7,298,890 B2 | 11/2007 | Massen | |
| 7,340,316 B2 | 3/2008 | Spaeth et al. | |
| 7,489,813 B2 | 2/2009 | Rutschmann et al. | |
| 7,661,170 B2 | 2/2010 | Goode et al. | |
| 7,735,237 B1 | 6/2010 | Moon | |
| 7,797,072 B2 | 9/2010 | Summit | |
| 7,896,827 B2 | 3/2011 | Ingimundarson et al. | |
| 8,005,651 B2 | 8/2011 | Summit et al. | |
| 8,059,917 B2 | 11/2011 | Dumas et al. | |
| 8,581,905 B2 | 11/2013 | Mitchell | |
| 8,739,428 B2 | 6/2014 | Emtman | |
| 8,988,503 B2 | 3/2015 | Pfeiffer et al. | |
| 9,149,224 B1 | 10/2015 | Newman et al. | |
| 2001/0002232 A1 | 5/2001 | Young et al. | |
| 2002/0016631 A1 | 2/2002 | Marchitto et al. | |
| 2002/0194023 A1 | 12/2002 | Turley et al. | |
| 2003/0032906 A1 | 2/2003 | Narula et al. | |
| 2003/0065259 A1 | 4/2003 | Gateno et al. | |
| 2004/0019266 A1 | 1/2004 | Marciante et al. | |
| 2004/0032595 A1 | 2/2004 | Massen | |
| 2004/0068337 A1 | 4/2004 | Watson et al. | |
| 2004/0088584 A1 | 5/2004 | Shachar et al. | |
| 2004/0133431 A1 | 7/2004 | Udiljak et al. | |
| 2004/0162511 A1 | 8/2004 | Barberio | |
| 2004/0230149 A1 | 11/2004 | Littlefield et al. | |
| 2004/0236424 A1 | 11/2004 | Berez et al. | |
| 2004/0260402 A1 | 12/2004 | Baldini et al. | |
| 2005/0004472 A1 | 1/2005 | Pratt | |
| 2005/0015172 A1 | 1/2005 | Fried et al. | |
| 2005/0031193 A1 | 2/2005 | Rutschmann et al. | |
| 2005/0043835 A1 | 2/2005 | Christensen | |
| 2005/0044740 A1 | 3/2005 | Hansen | |
| 2005/0061332 A1 | 3/2005 | Greenawalt et al. | |
| 2005/0065458 A1 | 3/2005 | Kim | |
| 2005/0256392 A1 | 11/2005 | Matory et al. | |
| 2006/0100832 A1 | 5/2006 | Bowman | |
| 2006/0161267 A1 | 7/2006 | Clausen | |
| 2007/0016323 A1 | 1/2007 | Fried | |
| 2007/0083384 A1 | 4/2007 | Geslak et al. | |
| 2007/0133850 A1 | 6/2007 | Paez | |
| 2007/0225630 A1 | 9/2007 | Wyatt et al. | |
| 2008/0120756 A1 | 5/2008 | Shepherd | |
| 2008/0124064 A1 | 5/2008 | Klinghult et al. | |
| 2008/0294083 A1 | 11/2008 | Chang et al. | |
| 2008/0319362 A1 | 12/2008 | Joseph | |
| 2009/0088674 A1 | 4/2009 | Caillouette et al. | |
| 2009/0254015 A1 | 10/2009 | Segal et al. | |
| 2010/0008588 A1 | 1/2010 | Feldkhun et al. | |
| 2010/0137770 A1 | 6/2010 | Ingimundarson et al. | |
| 2010/0138193 A1 | 6/2010 | Summit et al. | |
| 2010/0228646 A1 | 9/2010 | Heidel | |
| 2010/0268138 A1 | 10/2010 | Summit et al. | |
| 2011/0001983 A1 | 1/2011 | Becker et al. | |
| 2011/0056004 A1 | 3/2011 | Landi | |
| 2011/0092804 A1 | 4/2011 | Schoenefeld et al. | |
| 2011/0149094 A1 | 6/2011 | Chen et al. | |
| 2011/0166435 A1 | 7/2011 | Lye | |
| 2011/0248987 A1 | 10/2011 | Mitchell | |
| 2012/0098992 A1 | 4/2012 | Hosoe | |
| 2012/0165648 A1 | 6/2012 | Ferrantelli | |
| 2012/0235993 A1 | 9/2012 | Kim | |
| 2013/0123668 A1 | 5/2013 | Rodrigues Quintas et al. | |
| 2013/0301901 A1 | 11/2013 | Satish et al. | |
| 2014/0300722 A1 | 10/2014 | Garcia | |
| 2016/0317079 A1 | 11/2016 | Newman et al. | |
| 2017/0281009 A1 | 10/2017 | Obropta, Jr. et al. | |

OTHER PUBLICATIONS

"Digital Measuring System for Unloader & CTi CM Braces", Ossur; Aug. 1, 2012; 3 pages.

International Search Report and Written Opinion from International Application No. PCT/US13/56896, dated Apr. 23, 2014.

* cited by examiner

METHOD AND DEVICE FOR ORDERING A CUSTOM ORTHOPEDIC DEVICE

FIELD OF THE DISCLOSURE

The present disclosure relates to a method and device for ordering a custom orthopedic device including providing security provisions, receiving measurement information, capturing an image of the appropriate portion of the limb, and submitting ordering requests.

BACKGROUND

To provide customized support for a joint, a clinician may provide a patient with a custom fitted orthopedic device adapted to the specific anatomical dimensions of the individual patient. A common orthopedic device for customization is a knee brace. A patient will typically obtain a customized brace through a clinician having the expertise to assure that the orthopedic device fits the patient properly.

A clinician can prepare the brace himself, or order a custom orthopedic device remotely through the mail or by submitting an order over mail, phone, fax or the Internet. During the ordering process, the clinician typically provides the manufacturer or seller ("provider") with an image of a portion of the limb including the joint and measurements of the limb around the joint. The custom orthopedic brace is produced based on the submitted image of the limb and measurements. The provider may require the image of the limb be captured at a certain orientation, angle, height, and distance relative to the limb to ensure that the captured image accurately portrays the dimensions and proportions of the limb. Appropriate tags, reference indicia and reference markings of anatomy are often placed on the limb to identify the patient, the limb, and any other necessary information if the photo is misplaced from an order form.

It is undesirable for the picture to be taken when the camera is at an angle relative to the limb (angle normal to the line of progression of the limb) or when the limb is not aligned with the center of the image since such an image would inaccurately portray the dimensions and proportions of the limb. Producing a custom orthopedic brace based on such a misaligned image results in a poorly fitting brace. Likewise, poor resolution or lack of indicia applied on the limb may impede the producer in fully understanding the contours of the patient's limb.

Using a conventional camera, the photographer must estimate or otherwise measure the specified distance between the camera and the limb, the specified portion of the limb to capture in the image, and the appropriate orientation of the camera relative to the limb. Since the conventional camera does not provide feedback about the angle or orientation at which the camera is held, it is difficult for the photographer to determine whether the image of the limb being captured meets the requirements of the manufacturer or seller without additional aids.

The patient may need to use different devices to complete the entire ordering process. If the image of the limb is captured with a conventional digital camera, the image must then be transferred to a computer before the order and image can be uploaded over the Internet to the server of the manufacturer or seller.

While providing a photo is useful in understanding the patient's anatomy, dimensional measurements are likewise required. Various forms are required for completion by the clinician to determine measurement data and patient personal information. Other forms require the clinician to indicate brace models, features, accessories, colors, etc. From the requirement for forms and a photo, the ordering process both complicated and risks a mismatch of documents for the order.

The features of the disclosure provide a solution to the need to reduce image and limb misalignment and improve the ease of capturing an image of the limb and of ordering a custom orthopedic device without multiple forms.

SUMMARY

According to a method for ordering a custom orthopedic device for a joint, the method includes aligning a viewfinder image displayed on a screen and generated by an image sensor of a portable device with at least one predetermined portion of a limb including a joint. The method involves capturing and storing at least one image of the portion of the limb using the image sensor of the portable device based on at least one guideline. The at least one captured image is associated with measurements of the limb, and patient information entered into the portable device. The order is transmitted to the provider and contains the at least one captured image, the measurements of the limb, and the patient information from the portable device. The at least one guideline may be a depth of field guideline, a horizontal orientation guideline, a vertical orientation guideline, a tilt guideline, or a limb alignment guideline.

The at least one image of the limb may satisfy the depth of field guideline, the horizontal or the vertical orientation guideline, the tilt angle guideline, and the limb alignment guideline. The limb alignment guideline is a depth of field guideline overlaid on the viewfinder image. The depth of field guideline may be a reference frame for a first distance above a joint, a second distance below a joint, and a centering of the limb and joint in the captured image.

According to a variation, the first and second distances are the same and referenced from a knee axis line. The distances above and below the joint may be aligned with the depth of field guideline in the viewfinder image before capturing the image.

Once the orientation of the portable device relative to the limb satisfies the horizontal angle guideline or vertical angle guideline and the tilt angle guideline, the portable device enables image capture. The method may also include calibrating the image sensor of the portable device.

The method may include executing an ordering application, determining whether the ordering application has been previously executed. The image sensor may be calibrated upon the determination that the ordering application has not been previously executed. The image of the limb enables capture upon the determination that the ordering application has been previously executed.

The method may include reviewing the captured image of the limb and selecting a custom orthopedic device configuration. The step of reviewing the captured image of the limb includes viewing the captured image with an overlaid depth of field guideline to confirm the captured portion of the limb satisfies the overlaid depth of field guideline. The method may also include entering basic patient information into the portable device including measurements of the limb at various locations on the limb. The captured image may be overlaid with the basic patient information. The overlaid captured image may be stored in the portable device.

The method can involve configuring the custom orthopedic device, reviewing the order, and storing the order in a memory of the portable device. At least one previous order may be stored in the memory of the portable device. The order may be transmitted as an e-mail containing the patient information and the saved, captured image of the limb.

In an embodiment of the device, the device includes an image sensor configured to capture an image, a display, a gyroscope and/or accelerometer, a communication interface, a processor, and a memory. The processor is configured to enable capturing an image of a portion of a limb including a joint using the image sensor based on at least one guideline, and the image of the limb satisfies the at least one guideline. The gyroscope and/or accelerometer is configured to provide orientation data to the processor. The communication interface is configured to transmit an order containing the captured image and patient information from the apparatus over a network to a provider. The at least one guideline is at least one of a depth of field guideline, a horizontal orientation guideline, a vertical orientation guideline, a tilt guideline, or a limb alignment guideline.

The method may include a login page requiring clinician and patient input. Upon entry of the information on the login page, the user is directed to an order configuration home screen or page. From the home screen, the user may select many pages for making the customized order. The user may first select the image capture and input measurements, followed by entering patient information, orthopedic device (brace) configuration, and any other order information. The user is not limited to a sequence of page use, other than upon entry of all data fields and appropriate image capture, the order is sent to the provider.

The limb alignment guideline is a depth of field guideline overlaid on a viewfinder image. The depth of field guideline is a reference frame for a first distance above a joint, a second distance below a joint, and a centering of the limb and joint in the captured image. The processor is configured to provide an indication of the orientation of the device on the display. The processor is configured to calibrate the image sensor by setting the image sensor to a first resolution and a first zoom level. At least one image of anatomical landmarks or markings on the limb is captured. A three-dimensional model of the limb is generated from the markings along with circumferential measurements.

BRIEF DESCRIPTION OF THE DRAWINGS

The device and method for ordering a custom orthopedic device is described with reference to the accompanying drawings which show preferred embodiments according to the device described herein. It will be noted that the device as disclosed in the accompanying drawings is illustrated by way of example only. The various elements and combinations of elements described below and illustrated in the drawings can be arranged and organized differently to result in embodiments which are still within the spirit and scope of the device described herein.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. § 112, paragraph 6.

The embodiments of the method 2 and device 4 disclosed enable the user to easily capture accurate images of the limb and complete the ordering process on a single device. The method 2 may be implemented in an application executed on a portable device. The application guides the user through the ordering and image capturing process. Such a device and process reduces misalignment issues while integrating picture capturing and ordering into a single device.

The device used to capture the image and order the custom orthopedic brace may be any device having a display and an image sensor such as a mobile phone (iPhone®, Android® phone, Blackberry®, Windows® phone, etc.), a tablet (iPad®, Android® tablet, Windows® tablet etc.), a personal digital assistant (PDA), a computer, or any other portable device.

The preferred device 4 has an image sensor, a display, a processor, a gyroscope and/or accelerometer, memory, and a communication interface to allow communication of the order directly from the device over a network to a server of the manufacturer or seller.

Figure 1:
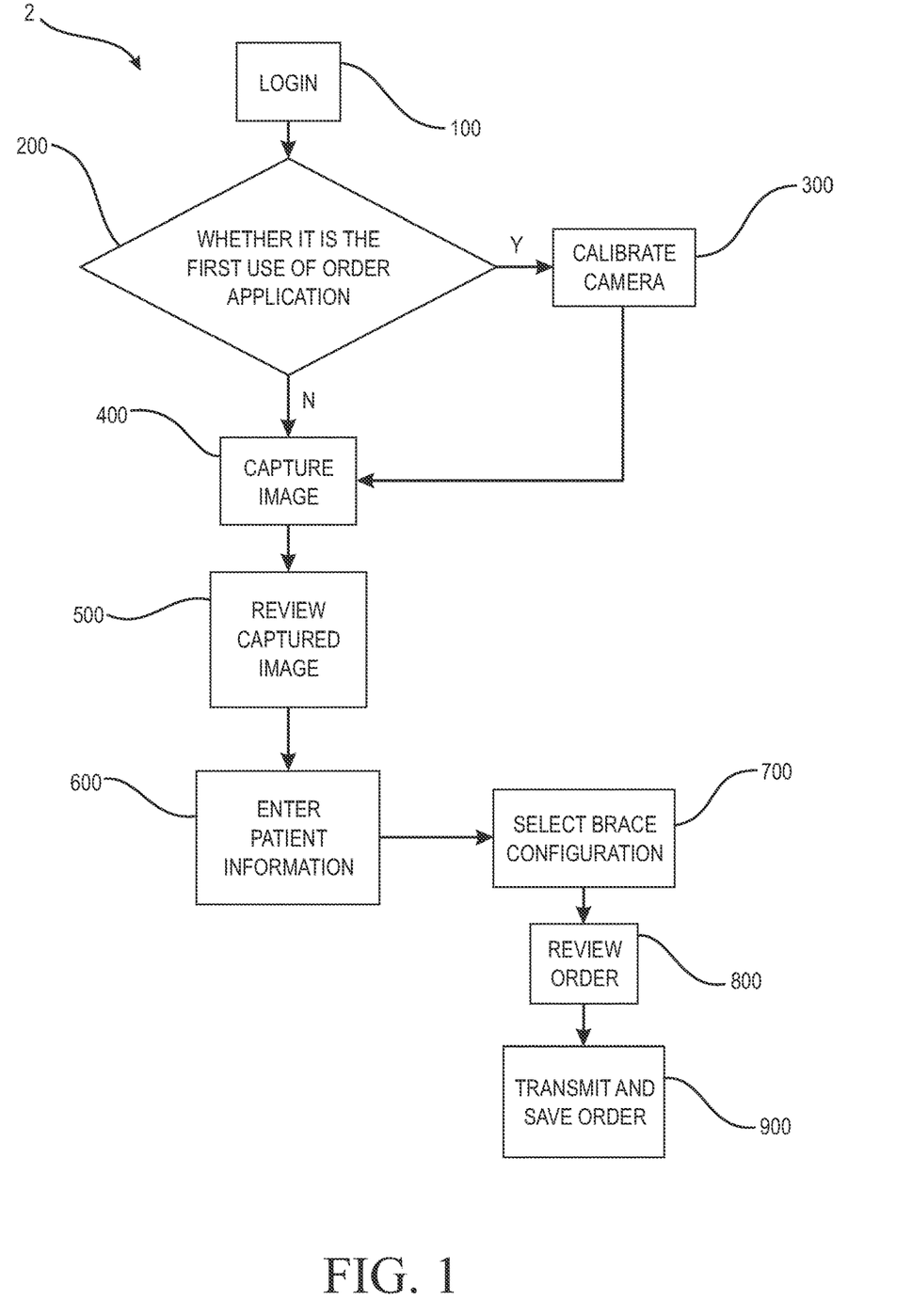
FIG. 1 is an overview of the steps in an embodiment of the custom orthopedic device ordering method.

FIG. 1 is an overview of an embodiment of a method 2 for ordering a custom orthopedic device. After the user selects the ordering application, the application is launched, and the application displays a login screen. At step 100, the user logs into an account or creates a new account using a keypad or similar on the device. The login page may include an option for an embedded tutorial including a visual step-by-step discussion stored on the device or available to the device through streaming. The tutorial may provide guidance on patient positioning, making anatomical landmarks on the limb, and taking circumferential measurements.

At step 200, the application determines whether the current session is the first use of the device 4 to order the custom orthopedic device. In one embodiment, if the current session is the first use, the application calibrates a camera of the device at 300. During calibration 300, the application automatically sets the camera to specific settings such as a specific resolution, zoom, and color setting.

Alternatively, the calibration 300 of the camera may be omitted. In this embodiment, the preferred camera settings are in text within the application, and the calibration is manually performed by the user by adjusting the settings of the camera. The preferred camera settings may be displayed during the image capturing process and during a review of the captured image. The preferred camera settings can also be displayed and included in a "help" section of the application.

If the current session is not the first use or calibration of the camera is unnecessary, the application enables capture of an image using guidelines and a specific alignment or orientation at step 400. In step 500, the captured image is reviewed by the user to determine whether the captured image meets the specified alignment. At step 600, patient information is entered, and a brace configuration is selected at 700. The user is prompted to review the order at 800 before the order is saved on the device and transmitted over a network to a server of the custom orthopedic device manufacturer or seller at 900.

Figure 2:
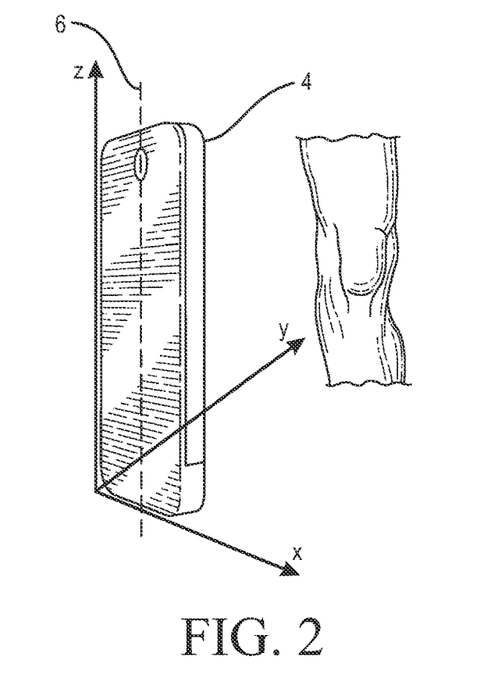
FIG. 2 shows a portrait orientation of a device for ordering the custom orthopedic device with respect to three axes.
Figure 3:
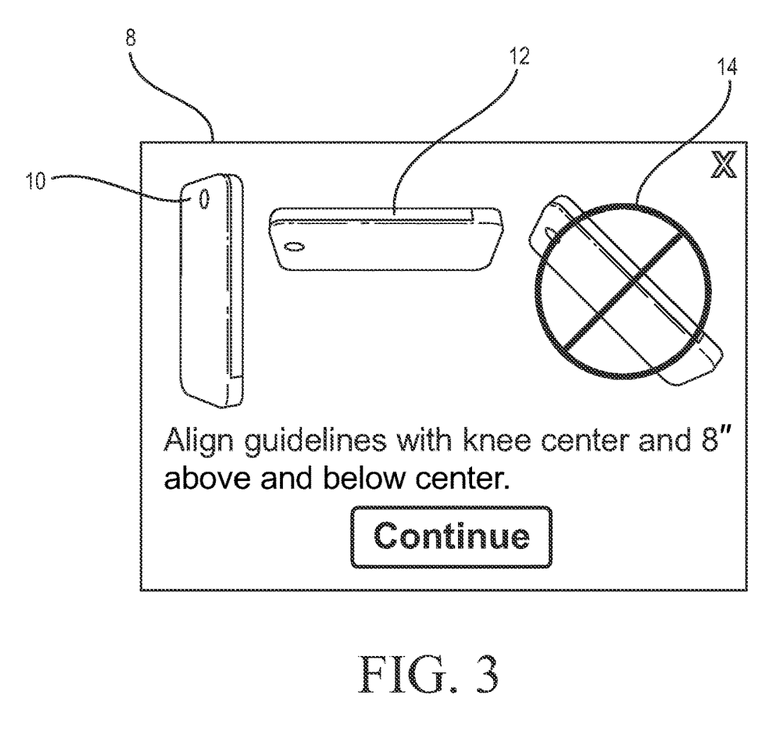
FIG. 3 is an example of the indication provided to the user of the preferred orientation of the device.
Figure 4:
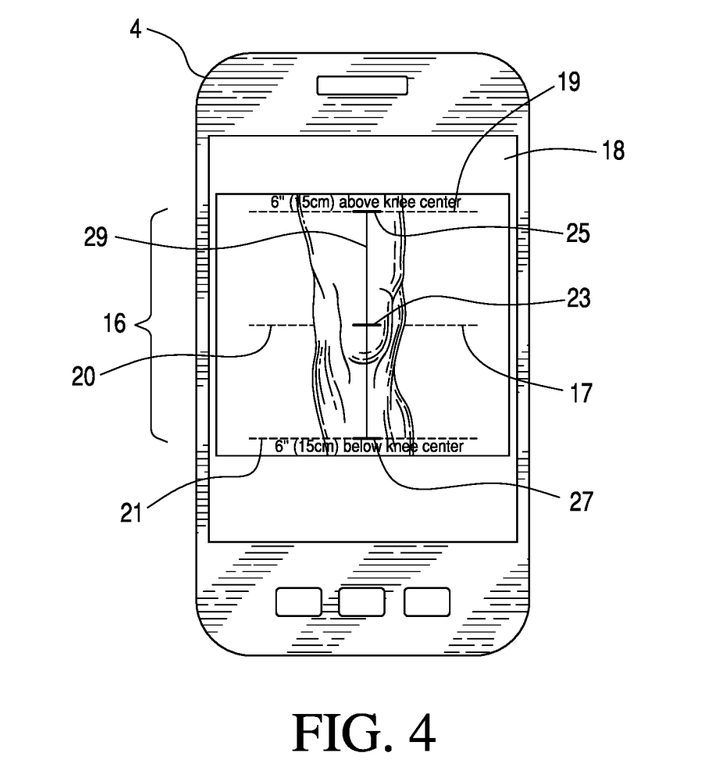
FIG. 4 shows the device having a viewfinder image overlaid with a depth of field guideline.

The capturing of the image of the limb at step 400 is described in more detail regarding FIGS. 2-4. Before the application enables capturing of an image, the application ensures the device 4 is properly aligned with the limb. To produce a properly aligned image of the limb, the joint is preferably centered in the image, and the image is captured from a point at the same height as the joint with the plane of the image being parallel to the limb or a vertical axis while the device 4 is in a portrait or landscape orientation. Where the horizontal axis is parallel to the x-axis, the y-axis represents depth, and the vertical axis is parallel to the z-axis, a longitudinal axis 6 of the device would be parallel to the horizontal axis when in a landscape orientation or to the vertical axis when in a portrait orientation.

In determining whether the device 4 is in an acceptable portrait or landscape orientation, the application uses the gyroscope and/or accelerometer of the device 4 to determine whether the orientation of the device 4 is within a certain degree range whether the longitudinal axis 6 of the device 4 is within five degrees of the horizontal axis or within five degrees of the vertical axis.

The application provides a visual indication 8 on a display 18 of the device 4 whether the device 4 is properly oriented and allows the user to adjust the device 4 until the orientation requirements are met.

FIG. 3 shows the device in a portrait orientation 10 followed by a landscape orientation 12 and an unacceptable tilted orientation 14. When the device is within the five degrees of the landscape or portrait orientation, the display will indicate by highlighting the landscape or portrait orientation in FIG. 3. If the device is not within five degrees of the vertical axis or the device is otherwise rotated about the vertical or horizontal axes, the cross-out symbol will flash to indicate to the user that adjustment of the device is tilted and adjustment is required.

Once the orientation requirements are met, the display shows the viewfinder image and enables capture of an image. The display 18 of the device 4 becomes the viewfinder for the camera and a depth of field guideline 16 is overlaid on the viewfinder image. The depth of field guideline 16 provides the user with assistance in centering the joint in the photo and capturing the appropriate portion of the joint. Before capturing the image of the limb, the limb may be measured and marked at multiple points to indicate specific distances above and below the joint, to aid in alignment with the depth of field guideline, and to provide reference points for circumference measurements of the limb. The markings may be at specific points or at regular intervals along and around the limb.

FIG. 4 shows an example of the depth of field guideline 16 on the display 18 of the device 4 to assist the user in capturing the appropriate portion of the limb. The portions 25, 27 of the leg about 15 cm above and below a knee axis 23 should be captured in the image for a custom knee brace. A hash mark 17 is provided at the center of the viewfinder image 20 to assist the user in aligning the joint with the center of the image. An upper guideline 19 is at the top of the viewfinder image 20 indicating that the distance of about 15 cm above the joint is aligned with the upper guideline 19. Similarly, a lower guideline 21 indicates the distance of about 15 cm below the joint is aligned with the lower guideline 21 in the image. The guideline 16, inclusive of mark and guidelines 17, 19, 21 may include a vertical line 29 on the center of the image to align with the center of the limb. While the depth of field guideline 16 for the knee defines a portion of the knee about 15 cm above and below the knee, the depth of field guideline 16 may define a portion of the limb any distance above and below a certain point.

To aid the user in correctly framing the limb in the picture, markings may first be placed on the limb indicating specific locations on the limb. An anatomical landmark or marking is placed at the point on the limb about 15 cm below the joint and about 15 cm above the joint which corresponds to the depth of field guidelines. Therefore, the photographer need only align the markings with the upper and lower guidelines and align the center hash mark over the center of the joint.

The method may require a delay before the image is taken to assure stable and clear focus. Upon alignment with the field guideline, the method requires a steady position before taking the image. A signal may be released, such as a green dot, to prompt the user to capture the image by pressing a button on the device.

In a variation, the clinician first identifies the medial joint space and marks it appropriately. The clinician then measures approximately 2 cm above the medial joint space and draws a line across the knee, from medial to lateral sides, to define the knee axis line. The clinician then identifies and marks the lateral joint space. The clinician then may measure and mark points both 7.5 cm and 15 cm above and below the knee axis line. The clinician marks the tibial peak below the 15 cm mark and the tibial peak above the 7.5 cm mark, and connects the two with a line.

Alternatively, the application may directly enable the capture of the image instead of checking the device orientation before enabling the display 18 to function as the viewfinder of the camera. The application may provide on-screen guides as to the current orientation of the device relative to the preferred orientation regarding each of the axes next to or over the viewfinder image.

In this manner, the application assists and guides the user in capturing the optimal image of the limb for a custom orthopedic device. Through immediate on-screen guidance as to the orientation of the device 4, the user can easily and quickly adjust the angle, orientation, and alignment of the device to obtain a well aligned and consistent photograph of the limb. The possibility of misalignment between the image capturing device and the limb is therefore greatly reduced.

According to a variation, the clinician takes both an anterior view of the limb with the markings, and a lateral view of the limb. In both instances, the depth of field guideline may vary according to the orientation of the limb, which is selected on the device by the clinician. The method may include image capture from any number sides of a patient's limb, including anterior, posterior, lateral and medial views and angles.

Once an image is captured, the user is prompted to review the captured image. During the review of the captured photograph at step 500, the captured image with the overlaid guidelines 16 is shown, and the user determines whether the correct portion of the limb is captured within the image and whether the limb is centered within the image. If the limb and the device 4 were not aligned when the image was captured, a new image may be taken. If a new image is captured, the application returns to step 400 to guide the user through the correct orientation and framing of the limb in the image. Once the photograph is confirmed, the user is prompted to enter measurements of the limb. The measurements of the limb may include the medial-lateral (M-L) width measurement of the limb and the circumference of the limb at various points above and below the joint. A measuring device such as a caliper or measuring tape may obtain the measurements of the limb.

Figure 5:
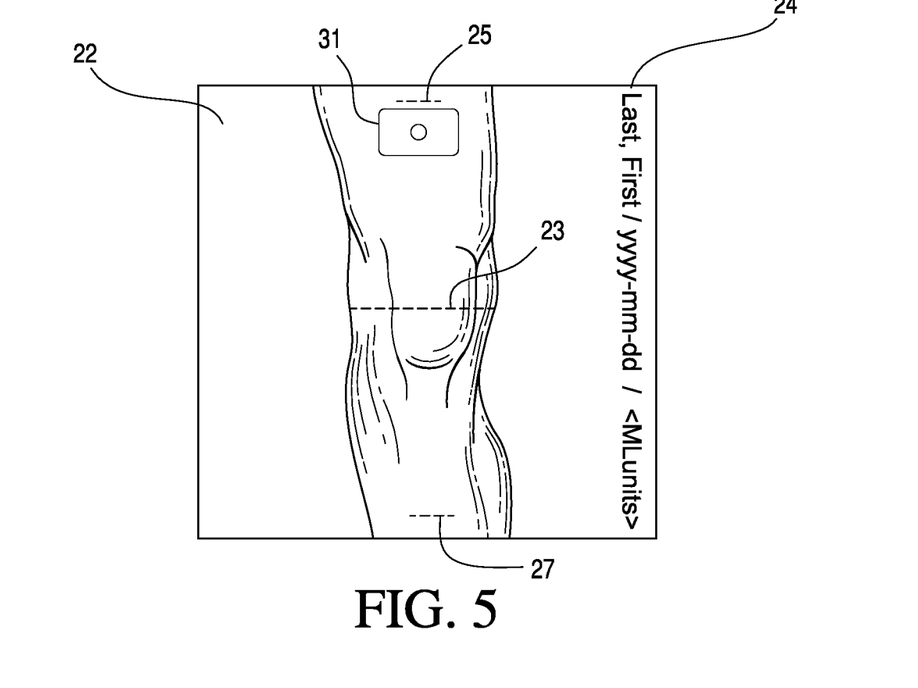
FIG. 5 is an example of the captured image stored with an identification label.

To associate the captured image 22 with the patient, the captured image 22 is stored with an identification label 24. The identification label 24 may be text overlaid on the captured image 22. FIG. 5 is an example of a saved image overlaid with an identification label 24. The information label 24 may include data such as the patient's name, date of the photograph, and the M-L measurement along one side of the image. The image with overlaid information is stored in the memory of the device. The image may be password protected or encrypted in the memory to protect the patient's privacy.

As shown in FIG. 5, the system may include a tilt indicator 31 arranged to allow the clinician to correctly orient the camera position. The tilt indicator 31 relies on a determination by the device to measure whether the angle or orientation of the device is proper to assure a successful captured image. In a preferred embodiment, the tilt indicator will display a red color when the device is not in the proper orientation to capture the image, and a green color when the device is in a proper orientation.

At 600, additional patient information is entered to fill out the order form. The patient information may include the name of the user, the prescriber of the orthopedic device, and the diagnosis or symptoms of the user with identification of the problem joint. After the patient information is entered, the application can create a partial order on the device in encrypted XML format including the captured photo and patient information. Other security measures may protect the patient's data under HIPAA regulations.

At step 700, the user or patient selects the appropriate orthopedic device configuration such as the orthopedic device model and color. The application guides the user through the different orthopedic devices and provides the user with options based on the selected orthopedic device. After selection and configuration of the orthopedic device, the partial order is saved. The user can enter a menu listing all orders saved on the device or continue to a review of the order. The list also indicates the status of the order such as whether the order has been transmitted to the maker or seller. If the user selects a link for an order not yet transmitted, the user is prompted to review the order.

At step 800, the order is displayed for review. The saved image and the collected information are displayed. The user can edit portions of the order with the changes made during the review being saved with the order. The user can also enter the clinician information and payment and shipping information. The user then may save the order or transmitting the order.

At step 900, the order is saved and/or transmitted to the server of the custom orthopedic device provider. The application sends the order in an e-mail and automatically populates the fields of the e-mail based on the data in the saved order. The patient information, brace information, and clinician or user information are inserted into the body of the e-mail while the saved image associated with the order is automatically attached to or inserted into the e-mail. When the user elects to send the e-mail containing the order information, the device can send the order directly to a server of the seller through a network. The application and/or the server may display or send a notification to the user to confirm the order.

While the embodiments described relate to a method and device for ordering a custom orthopedic device which can be accomplished with a single image, in another embodiment the method and device are used with or within a custom orthopedic device production method and system which produces the custom orthopedic device based on a three-dimensional model of the limb generated from a plurality of captured images.

To generate a three-dimensional model, markers or reference points are placed on the limb and are subsequently captured in the image. The markers or reference points assist in determining the dimensions of the limb from the image by providing information related to the surface of the limb. To place the markers or reference points on the limb, a sock or sleeve having markings may be worn on the limb or the limb may be marked at particular intervals. Markings can be contrasting colored markings in many shapes such as a circular shape, a rectangular shape, a triangular shape, or any combination and are preferably the same size. The distribution and density of the markings over the surface of the sock, sleeve, or limb varies depending on the type of limb and the desired three-dimensional modeling resolution.

Providing more markings or a higher density of markings in a certain area produces a more accurate three-dimensional model of the limb since more reference points would be provided in the captured image. The markings may be concentrated in areas where there are more variations in the continuity of the limb surface such as around the joint area. Additional references may be added to the limb or the sock. In ordering a custom knee brace, additional markings or references are added to indicate the center of the knee, the angle of the tibia, and the locations of the condyles.

Figure 6:
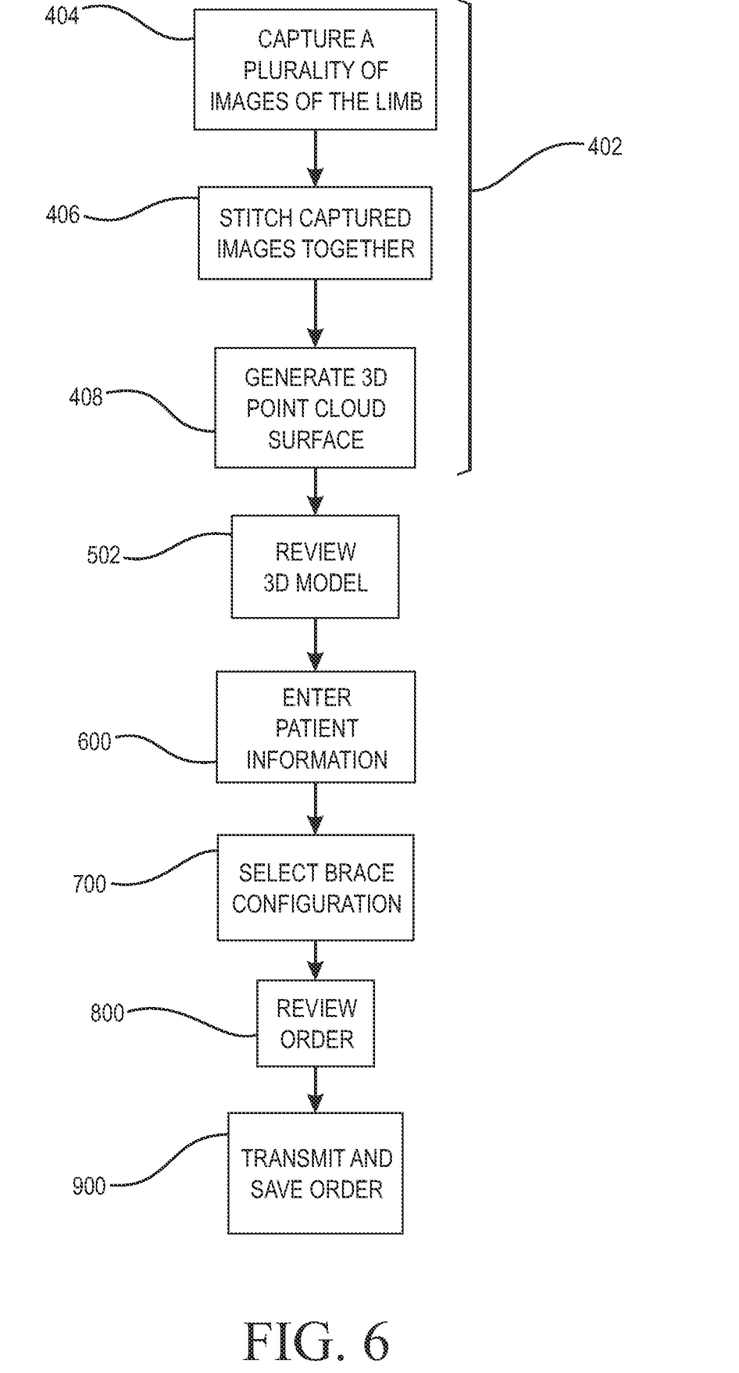
FIG. 6 illustrates is a flowchart of an embodiment of the custom orthopedic device ordering method using a three-dimensional model of the limb.

FIG. 6 shows an image capturing process 402 and a review stage 502 in an embodiment of the method for ordering a custom orthopedic device where a three-dimensional image of the limb is captured. This embodiment follows the same steps as the embodiment in FIG. 1 and differs in the specific steps taken to capture the image at 400 and in the image displayed during the review stage 500 of the embodiment of FIG. 1. After the three-dimensional model specific steps of 402 and 502, the ordering process continues with the remaining general ordering steps 600, 700, 800, and 900 as described with respect to FIG. 1.

Once the ordering application is executed and before the image capturing step 400, the user is prompted to select whether to use a three-dimensional model. If the user does not select the three-dimensional model, the method continues as described regarding FIGS. 1-5. If the user uses the three-dimensional option, the image capturing process 402 as shown in FIG. 6 and review process 502 are used.

Before beginning the image capturing process 402, markings or reference points are added to the limb in the manner described. In the image capturing process 402 starting with step 404, the photographer captures at least two images of the limb at various angles or views. Preferably, at least four individual images are captured of the limb with each image capturing a different angle or view of the limb such that the entire circumference of the appropriate portion of the limb is captured within the plurality of images. The application may instruct the user to capture a certain number of images of the limb from different angles, orientations, heights, or different portions of the limb.

Alternatively, the application may use continuous image capturing where the application automatically captures images at different intervals such that the photographer need only move the device and indicate when images of all views or sides of the limb have been captured.

During the image capturing process 402, the application can guide the photographer in capturing the appropriate angles or views of the limb with the appropriate alignment of the limb in the image using accelerometer and/or gyroscope data from the device using the guidelines described. Depending on the depth of field of the images, the application can determine the appropriate number of images, angles, or views needed to generate an accurate three-dimensional model of the limb.

At step 406, the application analyzes and processes the plurality of captured images to stitch the images together and form a continuous view of the limb. The application can perform the stitching of the images together automatically or with user assistance. The stitching of the images can also be performed while the images are being captured or with the plurality of individual separately captured images.

At 408, from the stitched image, the application generates a three-dimensional model of the limb using the markings on the sock, sleeve, or limb. The model may be a computer-aided design (CAD) point cloud surface where the markings shown in the captured images translate into points in the point could surface. The application preferably generates a 360° view of the limb.

Once the image capturing process 402 is completed, the application prompts the user to review the generated three-dimensional model to ensure that the three-dimensional model accurately depicts the surface shape of the corresponding portion of the limb at 502. During review of the three-dimensional model, the user can rotate and zoom into the model to view all sides of and different levels of detail of the limb. The user is given the option of approving the generated model or re-capturing the limb to generate a more accurate model.

If the user performs the image capturing process 402 again, the current generated model may be saved for comparison with later models during the review stage. If the user approves of the generated model, the application continues with the general ordering process stages 600-900 as described regarding FIG. 1. For the order review at 800 and transmission and saving of the order 900, the order can include the plurality of images and/or the three-dimensional model of the limb.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, or a combination, all of which are behaviorally equivalent. Modules may be implemented using computer hardware in combination with software routine(s) written in a computer language (such as C, C++, Fortran, Java, Basic, Matlab or the like). It may be possible to implement modules using physical hardware that incorporates discrete or programmable analog and/or digital hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. Finally, the above mentioned technologies may be used in combination to achieve the result of a functional module.

The application may be software embodied on a computer readable medium which when executed by a processor of a computer performs a sequence of steps. A computer readable medium may be a floppy disk, a flexible disk, a hard disk, magnetic tape, or any other magnetic medium, a CD-ROM, any other optical medium, a RAM, a ROM, or any other medium from which a computer can read. Various forms of computer readable media may carry one or more sequences of one or more instructions to a processor for execution. The software may be transmitted over a wired or wireless network to the device.

While the foregoing steps embodiments have been described and shown, alternatives and modifications of these embodiments, such as those suggested by others, may be made to fall within the scope of the invention. A preferred order for the steps in the method of ordering the custom orthopedic device has been described. It is noted that the order of the steps in the method may be rearranged.

The invention claimed is:

1. A device for ordering a custom orthopedic device, comprising:

an image sensor configured to capture a first image of a portion of a limb and to generate a viewfinder image;

a display configured to show a first depth of field guideline overlaid on the viewfinder image;

a processor configured to enable capturing the first image of the portion of the limb using the image sensor after the device has been positioned relative to the portion of the limb such that the first image satisfies the first depth of field guideline;

the first depth of field guideline comprising first and second guidelines corresponding respectively to first and second predetermined distances above and below a predetermined part of the portion of the limb, the first image satisfies the first depth of field guideline when the first and second guidelines of the first depth of field guideline in the viewfinder image are respectively aligned prior to image capture to the first and second predetermined distances above and below the predetermined part of the portion of the limb, respectively;

the first and second predetermined distances above and below the predetermined part of the portion of the limb are marked on the limb prior to image capture; and a communication interface configured to transmit an order containing the captured first image and patient information;

wherein the processor is further configured to guide a user to capture a plurality of images of the portion of the limb using the image sensor;

wherein an entire circumference of the portion of the limb is captured from the plurality of images;

wherein the processor is further configured for stitching the plurality of images together to define a continuous view of the portion of the limb.

2. The device for ordering a custom orthopedic device of claim 1, wherein the processor is configured to enable capturing at least two two images of the portion of the limb using the image sensor after the device has been positioned relative to the portion of the limb such that each image of the plurality of images satisfies a corresponding depth of field guideline of a plurality of depth of field guidelines, respectively.

3. The device for ordering a custom orthopedic device of claim 1, wherein the processor is further configured to enable capturing the plurality of images of the portion of the limb using the image sensor after the device has been positioned relative to the portion of the limb such that the plurality of images are within a certain degree range of a landscape or a portrait orientation as determined by a gyroscope and/or accelerometer of the device for ordering a custom orthopedic device.

4. The device for ordering a custom orthopedic device of claim 3, wherein the processor is configured to highlight the landscape or the portrait orientation on the display upon the gyroscope and/or the accelerometer determining that the device is within the certain degree range of the landscape or the portrait orientation, and to provide a notification on the display if the device is outside the certain degree range.

5. The device for ordering a custom orthopedic device of claim 1, wherein the processor is further configured to allow a user to recapture one or more images of the plurality of images after reviewing the continuous view of the portion of the limb.

6. The device for ordering a custom orthopedic device of claim 1, wherein the portion of the limb is a knee.

7. The device for ordering a custom orthopedic device of claim 2, wherein the processor is configured to automatically capture at least one image of the plurality of images.

8. A method for ordering a custom orthopedic device, the method comprising the steps:
providing a device comprising:
an image sensor configured to capture a first image of a portion of a limb and to generate a viewfinder image;
a display configured to show a first depth of field guideline overlaid on the viewfinder image;
a processor configured to enable capturing the first image of the portion of the limb using the image sensor after the device has been positioned relative to the portion of the limb such that the first image satisfies the first depth of field guideline;
the first depth of field guideline comprising first and second guidelines corresponding respectively to first and second predetermined distances above and below a predetermined part of the portion of the limb, the first image satisfies the first depth of field guideline when the first and second guidelines of the first depth of field guideline in the viewfinder image are respectively aligned prior to image capture to the first and second predetermined distances above and below the predetermined part of the portion of the limb, respectively;
a communication interface configured to transmit an order containing the captured first image and patient information;
marking the portion of the limb at at least the first and second predetermined distances; and
capturing the first image of the marked portion of the limb using the image sensor;
providing a sleeve with a plurality of markings, the markings varying in density according to variations in a continuity of a surface of the portion of the limb;
capturing two, three, or four images of the portion of the limb using the image sensor after the device has been positioned relative to the portion of the limb such that the two, three, or four images satisfy a second, third, and/or fourth depth of field guideline, respectively, the first, second, third, and/or fourth depth of field guidelines configured to together capture an entire circumference of the portion of the limb.

9. The method for ordering a custom orthopedic device of claim 8, the method further comprising the step of prompting a user to review the captured first image.

10. The method for ordering a custom orthopedic device of claim 8, wherein the portion of the limb is a knee, the method further comprising the step of marking at least a medial or a lateral joint space of the knee.

11. The method for ordering a custom orthopedic device of claim 10, further comprising the step of marking a knee axis line above the medial joint space.

12. The method for ordering a custom orthopedic device of claim 11, further comprising the step of marking the portion of the limb approximately 7.5 cm and 15 cm above and below the knee axis line.

13. The method for ordering a custom orthopedic device of claim 8, further comprising the step of marking the portion of the limb at or with at least one of an angle of a tibia, a location of one or more condyle, and a line between tibial peaks.

14. The method for ordering a custom orthopedic device of claim 8, wherein the step of marking the portion of the limb at at least the first and second predetermined distances is performed over the sleeve.

\* \* \* \* \*